(12) United States Patent
Dannenberg

(10) Patent No.: US 6,486,203 B1
(45) Date of Patent: Nov. 26, 2002

(54) TREATING INFLAMMATORY DISEASES OF THE HEAD AND NECK WITH CYCLOOXYGENASE-2 INHIBITORS

(75) Inventor: Andrew J. Dannenberg, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/762,286

(22) PCT Filed: Jul. 29, 1999

(86) PCT No.: PCT/US99/16685

§ 371 (c)(1),
(2), (4) Date: Feb. 7, 2001

(87) PCT Pub. No.: WO00/13685

PCT Pub. Date: Mar. 16, 2000

Related U.S. Application Data

(60) Provisional application No. 60/099,343, filed on Sep. 8, 1998.

(51) Int. Cl.[7] .................. A61K 31/34; A61K 31/415; A61K 31/045; A61K 31/05
(52) U.S. Cl. ................. 514/473; 514/406; 514/403; 514/730; 514/734
(58) Field of Search ................. 514/473, 406, 514/403, 730, 734

(56) References Cited

U.S. PATENT DOCUMENTS

| | | | |
|---|---|---|---|
| 4,870,210 A | 9/1989 | Musser ...................... 564/228 |
| 5,436,265 A | 7/1995 | Black et al. ................. 514/420 |
| 5,466,823 A | 11/1995 | Talley et al. ............. 548/377.1 |
| 5,633,272 A | 5/1997 | Talley et al. ................ 514/378 |
| 5,698,584 A | * 12/1997 | Black et al. ................. 514/462 |
| 5,710,181 A | 1/1998 | Williamson et al. ........ 514/634 |
| 6,048,850 A | 4/2000 | Young et al. ................ 514/183 |

OTHER PUBLICATIONS

Kawamori, T., et al., Cancer Research 58, 409–412 (Feb. 1, 1998).

Subbaramaiah, K., et al., J. Biol. Chem. 273, 21875–21882 (1998).

* cited by examiner

*Primary Examiner*—Theodore J. Criares
*Assistant Examiner*—Jennifer Kim

(57) ABSTRACT

A patient with an inflammatory disease of the head and neck is treated with a therapeutic amount of a selective inhibitor of cyclooxygenase-2 or a cyclooxygenase-2 inhibitor from a natural source. In one embodiment, a patient with a sore throat caused by tonsillitis or pharyngitis is treated with the topical application of a cyclooxygenase-2 inhibitor from a natural source. In other embodiments, patients with sore throat caused by tonsillitis or pharyngitis or a patient with sinusitis are treated by systemic administration of a selective inhibitor of cyclooxygenase-2. In another embodiment, a patient with periodontitis is treated by administration of a cyclooxygenase-2 inhibitor from a natural source.

17 Claims, No Drawings

TREATING INFLAMMATORY DISEASES OF THE HEAD AND NECK WITH CYCLOOXYGENASE-2 INHIBITORS

CROSS-REFERENCE TO RELATED APPLICATIONS

This application is a filing under 35 U.S.C. 371 of PCT/US99/16685 Jul. 29, 1999 which claims the benefit of U.S. Provisional Application No. 60/099,343, filed on Sep. 8, 1998, and incorporates by reference the entire disclosure of U.S. Provisional Application No. 60/099,343; PCT/US99/16685 has been published under No. WO 00/13685, and the publication is in English.

The invention was made at least in part with United States Government support under National Institutes of Health grant CA 68136. The United States Government has certain rights in the invention.

TECHNICAL FIELD

The invention herein is directed to an expansion of the use of selective inhibitors of cyclooxygenase-2 and of natural substances which inhibit cyclooxygenase-2.

BACKGROUND OF THE INVENTION

Prostaglandins are important mediators of inflammation that are produced at elevated levels in inflamed tissues. The increased amounts of prostaglandins produced in inflamed tissues reflect enhanced synthesis, which occurs by cyclooxygenase-catalyzed metabolism of arachidonic acid. Two different isoforms of cyclooxygenase (COX) designated cyclooxygenase-1 (COX-1) and cyclooxygenase-2 (COX-2) have been identified. COX-1 is a constitutive isoform present in most tissues. COX-2 is not detectable in most normal tissues, but it is induced by cytokines, growth factors, oncogenes and tumor promoters. The increased production of prostaglandins in the joints of patients with rheumatoid arthritis has been attributed to elevated levels of COX-2.

Traditional nonsteroidal anti-inflammatory drugs (NSAIDs) such as aspirin inhibit the activities of COX-1 and COX-2 and therefore the synthesis of pro-inflammatory prostaglandins. NSAID-mediated inhibition of COX-1 is believed to be responsible for side effects such as peptic ulcer disease. Selective inhibitors of COX-2 have been developed in an effort to decrease the side effects of traditional NSAIDs. In fact, selective inhibitors of COX-2 do appear to be very effective inhibitors of rheumatoid arthritis while causing fewer gastrointestinal side effects than traditional NSAIDs.

While aspirin has been used to treat sore throat, heretofore there has been no proof that COX-2 is upregulated in sore throat and no suggestion of the use of selective inhibitors of COX-2 or of use of COX-2 inhibitors from natural sources, to treat sore throat.

While nitric oxide synthase inhibitors have been suggested for treating acute and chronic inflammatory diseases including sinusitis (see Williamson et al. U.S. Pat. No. 5,710,181), heretofore there has been no description of the use of selective inhibitors of COX-2 or of the use of COX-2 inhibitors from natural sources, to treat sinusitis.

SUMMARY OF THE INVENTION

The invention herein is directed to a method for treating a patient with an inflammatory disease of the head and neck comprising administering to said patient a therapeutic amount of a selective inhibitor of cyclooxygenase-2 or of a cyclooxygenase-2 inhibitor from a natural source.

The term "inflammatory disease of the head and neck" includes, without limitation, sore throat, e.g., that caused by tonsillitis or pharyngitis, and sinusitis.

The term "tonsillitis" is used herein to mean an acute inflammation of the palatine tonsils and includes tonsillitis caused by bacterial and viral infections.

The term "pharyngitis" is used herein to mean an acute inflammation of the pharynx and includes pharyngitis caused by bacterial and viral infections.

The term "sinusitis" is used herein to mean an inflammatory process in the paranasal sinuses and includes such condition caused by viral, bacterial and fungal infections or allergic reactions.

The term "inhibitor of cyclooxygenase-2" is used herein to mean a compound which directly inhibits cyclooxygenase-2 metabolized catalysis of arachidonic acid and/or inhibits the transcription of cyclooxygenase-2 and excludes nitric oxide synthase inhibitors. The term includes competitive inhibitors as well as non-competitive inhibitors.

The term "selective inhibitor of cyclooxygenase-2" is used herein to mean compound which selectively inhibits cyclooxygenase-2 in preference to cyclooxygenase-1 and particularly compound for which the ratio of the $IC_{50}$ concentration (concentration inhibiting 50% of activity) for cyclooxygenase-1 to the $IC_{50}$ concentration for cyclooxygenase-2 is greater than 1. Such ratio is readily determined by assaying for cyclooxygenase-2 activity and assaying for cyclooxygenase-1 activity by the methods set forth at column 39, line 55—column 40, line 36 of Talley et al. U.S. Pat. No. 5,633,272, which is incorporated herein by reference, and from the resulting data obtaining a ratio of $IC_{50}$s.

The term "natural source" in the phrase "cyclooxygenase-2 inhibitor from a natural source" is a plant, marine or animal organism.

DETAILED DESCRIPTION

We turn firstly to the selective inhibitors of cyclooxygenase-2. The selective inhibitors of cyclooxygenase-2 are synthetic compounds.

The selective inhibitors of cyclooxygenase-2 are preferably those where the ratio of the $IC_{50}$ concentration for cyclooxygenase-1 to the $IC_{50}$ concentration for cyclooxygenase-2 is 100 or more.

Selective inhibitors of cyclooxygenase-2 include the following compounds:

(1) 4-[5-(4-Chlorophenyl)-3-(trifluoromethyl)-1H-pyrazol-1-yl]benzenesulfonamide
(2) 4-[5-(4-Bromophenyl)-3-(trifluoromethyl)-1H-pyrazol-1-yl]benzenesulfonamide
(3) 4-[5-(3-Chlorophenyl)-3-(trifluoromethyl)-1H-pyrazol-1-yl]benzenesulfonamide
(4) 4-[5-(4-Methylphenyl)-3-(trifluoromethyl)-1H-pyrazol-1-yl]benzenesulfonamide
(5) 4-[5-(2-Chlorophenyl)-3-(trifluoromethyl)-1H-pyrazol-1-yl]benzenesulfonamide
(6) 4-[5-(4-Trifluoromethylphenyl)-3-(trifluoromethyl)-1H-pyrazol-1-yl]benzenesulfonamide
(7) 4-[5-(4-Fluorophenyl)-3-(trifluoromethyl)-1H-pyrazol-1-yl]benzenesulfonamide
(8) 4-[5-Phenyl-3-(trifluoromethyl)-1H-pyrazol-1-yl]benzenesulfonamide (9) 4-[5-(4-Methoxyphenyl)-3-(trifluoromethyl)-1H-pyrazol-1-yl]benzenesulfonamide
(10) 4-[5-(4-Trifluoromethoxyphenyl)-3-(trifluoromethyl)-1H-pyrazol-1-yl]benzenesulfonamide
(11) 4-[5-(2-Methylphenyl)-3-(trifluoromethyl)-1H-pyrazol-1-yl]benzenesulfonamide
(12) 4-[5-(4-Chlorophenyl)-3-(difluoromethyl)-1H-pyrazol-1-yl]benzenesulfonamide
(13) 4-[4-(Aminosulfonyl)phenyl]-5-(4-chlorophenyl)-1H-pyrazol-3-carboxylate
(14) 4-[4-(Aminosulfonyl)phenyl]-5-(4-chlorophenyl)-1H-pyrazol-3-carboxamide
(15) 4-[5-(4-[Methylthio]phenyl)-3-(difluoromethyl)-1H-pyrazol-1-yl]benzenesulfonamide
(16) 4-[5-(4-[Methylsulfonyl]phenyl)-3-(difluoromethyl)-1H-pyrazol-1-yl]benzenesulfonamide
(17) 4-[5-(2,4-[Difluoro]phenyl)-3-(trifluoromethyl)-1H-pyrazol-1-yl]benzenesulfonamide
(18) 4-[5-(2,6-[Difluoro]phenyl)-3-(trifluoromethyl)-1H-pyrazol-1-yl]benzenesulfonamide
(19) 4-[5-(4-Cyanophenyl)-3-(trifluoromethyl)-1H-pyrazol-1-yl]benzenesulfonamide
(20) 4-[5-(4-Chlorophenyl)-3-(heptafluoropropyl)-1H-pyrazol-1-yl]benzenesulfonamide
(21) 4-[5-(4-Chlorophenyl)-3-(chloro-difluoromethyl)-1H-pyrazol-1-yl]benzenesulfonamide
(22) 4-[5-(4-Chlorophenyl)-3-(pentafluoroethyl)-1H-pyrazol-1-yl]benzenesulfonamide
(23) 4-[5-(4-Biphenyl)-3-(difluoromethyl)-1H-pyrazol-1-yl]benzenesulfonamide
(24) 4-[5-(4-Pyrazinyl)-3-(difluoromethyl)-1H-pyrazol-1-yl]benzenesulfonamide
(25) 4-[5-(5-Chloro-2-thienyl)-3-(difluoromethyl)-1H-pyrazol-1-yl]benzenesulfonamide
(26) 4-[5-(4-Morpholino)phenyl)-3-(difluoromethyl)-1H-pyrazol-1-yl]benzenesulfonamide
(27) 4-[5-(1-Cyclohexyl-3-(difluoromethyl)-1H-pyrazol-1-yl]benzenesulfonamide
(28) 4-[5-(5-Bromo-2-thienyl)-3-(difluoromethyl)-1H-pyrazol-1-yl]benzenesulfonamide
(29) 4-[5-(4-Thienyl)-3-(difluoromethyl)-1H-pyrazol-1-yl]benzenesulfonamide
(30) 4-[5-(4-[Trifluoromethyl]phenyl)-3-(difluoromethyl)-1H-pyrazol-1-yl]benzenesulfonamide
(31) 4-[5-(3,4-Dichlorophenyl)-3-(trifluoromethyl)-1H-pyrazol-1-yl]benzenesulfonamide
(32) 4-[5-(2,4-Dichlorophenyl)-3-(trifluoromethyl)-1H-pyrazol-1-yl]benzenesulfonamide
(33) 4-[5-Phenyl-3-(3-hydroxypropyl)-1H-pyrazol-1-yl]benzenesulfonamide
(34) 4-[5-(4-Fluorophenyl)-3-(3-hydroxypropyl)-1H-pyrazol-1-yl]benzenesulfonamide
(35) 4-[4-(Aminosulfonyl)phenyl]-5-(4-fluorophenyl)-1H-pyrazole]-3-propanoic acid
(36) 4,5-Dihydro-4-[3-trifluoromethyl]-1H-benz[g]indazol-1-yl]benzenesulfonamide
(37) 4-[5-(4-Chlorophenyl)-4-chloro-1H-pyrazol-1-yl]benzenesulfonamide
(38) 4-[5-(4-Chlorophenyl)-3-(trifluoromethyl)-4-chloro-1H-pyrazol-1-yl]benzenesulfonamide
(39) 4-[1-(4-Fluorophenyl)-3-(trifluoromethyl)-1H-pyrazol-5-yl]benzenesulfonamide
(40) 1-(2,4,6-Trichlorobenzoyl)-5-methoxy-2-methyl-3-indolyl acetic acid
(41) 1-(2,6-dichlorobenzoyl)-5-methoxy-2-methyl-3-indolyl acetic acid
(42) 3-(4-Aminosulfonyl)phenyl)-2-(4-fluorophenyl)-5-(2-hydroxy-2-propyl)thiophene
(43) 3-(4-(Aminosulfonyl)phenyl-2-(4-fluorophenyl-thiophene
(44) 3-(4-(Aminosulfonyl)phenyl)-2-(4-fluorophenyl)-5-(2-propyl)thiophene
(45) 3-(4-(Aminosulfonyl)phenyl)-2-cyclohexylthiophene
(46) 5-(4-Carboxyphenyl)-4-(4-(methylsulfonyl)phenyl)thiophene-2-carboxylic acid
(47) 4-(4-Fluorophenyl)-2-methyl-5-(4-(methylsulfonyl)phenyl)thiazole
(48) 2-(4-Fluorophenyl)-3-(4-methylsulfonyl)phenyl)-2-cyclopenten-1-one
(49) 4-(4-(Methylsulfonyl)phenyl-5-(4-fluorophenyl)-isothiazole
(50) 3-(4-Fluorophenyl)-4-(4-(methylsulfonyl)phenyl-2-(5H)-furanone
(51) 3-(4-Fluorophenyl)-4-(4-(aminosulfonyl)phenyl)-2-(2H)-furanone
(52) 3-(4-Fluorophenyl)-4-(4-(methylsulfonyl)phenyl)furan
(53) 5,5-Dimethyl-3-(4-fluorophenyl)-4-(4-methylsulfonyl-phenyl)-2-(5H)furanone
(54) 2-((4-Aminosulfonyl)phenyl)-3-(4-fluorophenyl)thiophene
(55) 3-(2,4-Difluorophenyl)-4-(4-(methylsulfonyl)phenyl)-2-(5H)-furanone
(56) 3-(3,4-Difluorophenyl)-4-(4-(methylsulfonyl)phenyl)-2-(5H)-furanone
(57) 3-(2,6-Difluorophenyl)-4-(4-(methylsulfonyl)phenyl)-2-(5H)-furanone
(58) 3-(2,5-Difluorophenyl)-4-(4-(methylsulfonyl)phenyl)-2-(5H)-furanone
(59) 3-(3,5-Difluorophenyl)-4-(4-(methylsulfonyl)phenyl)-2-(5H)-furanone
(60) 3-(4-Bromophenyl)-4-(4-(methylsulfonyl)phenyl)-2-(5H)-furanone
(61) 3-(4-Chlorophenyl)-4-(4-(methylsulfonyl)phenyl)-2-(5H)-furanone
(62) 3-(4-Methoxyphenyl)-4-(4-(methylsulfonyl)phenyl)-2-(5H)-furanone
(63) 3-(Phenyl)-4-(4-(methylsulfonyl)phenyl)-2-(5H)-furanone
(64) 3-(2-Chlorophenyl)-4-(4-(methylsulfonyl)phenyl)-2-(5H)-furanone
(65) 3-(2-Bromo-4-fluorophenyl)-4-(4-(methylsulfon-yl)phenyl)-2-(5H)-furanone
(66) 3-(2-Bromo-4-Chlorophenyl)-4-(4-(methylsulfon-yl)phenyl)-2-(5H)-furanone
(67) 3-(4-Chloro-2-fluorophenyl)-4-(4-(methylsulfonyl)phenyl)-2-(5H)-furanone
(68) 3-(3-Bromo-4-fluorophenyl)-4-(4-(methylsulfonyl)phenyl)-2-(5H)-furanone
(69) 3-(3-Chlorophenyl)-4-(4-(methylsulfonyl)phenyl)-2-(5H)-furanone
(70) 3-(2-Chloro-4-fluorophenyl)-4-(4-(methylsulfonyl)phenyl)-2-(5H)-furanone
(71) 3-(2,4-Dichlorophenyl)-4-(4-(methylsulfonyl)phenyl)-2-(5H)-furanone
(72) 3-(3,4-Dichlorophenyl)-4-(4-(methylsulfonyl)phenyl)-2-(5H)-furanone
(73) 3-(2,6-Dichlorophenyl)-4-(4-(methylsulfonyl)phenyl)-2-(5H)-furanone
(74) 3-(3-Chloro-4-fluorophenyl)-4-(4-(methylsulfonyl)phenyl)-2-(5H)-furanone
(75) 3-(4-Trifluoromethylphenyl)-4-(4-(methylsulfonyl)phenyl)-2-(5H)-furanone
(76) 3-(3-Fluoro-4-methoxyphenyl)-4-(4-(methylsulfonyl)phenyl)-2-(5H)-furanone
(77) 3-(3-Chloro-4-methoxyphenyl)-4-(4-(methylsulfonyl)phenyl)-2-(5H)-furanone

(78) 3-(3-Bromo-4-methoxyphenyl)-4-(4-(methylsulfonyl)phenyl)-2-(5H)-furanone
(79) 3-(2-Fluorophenyl)-4-(4-(methylsulfonyl)phenyl)-2-(5H)-furanone
(80) 3-(4-Methylthiophenyl)-4-(4-(methylsulfonyl)phenyl)-2-(5H)-furanone
(81) 3-(3-Fluorophenyl)-4-(4-(methylsulfonyl)phenyl)-2-(5H)-furanone
(82) 3-(2-Chloro-6-fluorophenyl)-4-(4-(methylsulfonyl)phenyl)-2-(5H)-furanone
(83) 3-(3-Bromo-4-methylphenyl)-4-(4-(methylsulfonyl)phenyl)-2-(5H)-furanone
(84) 3-(4-Bromo-2-fluorophenyl)-4-(4-(methylsulfonyl)phenyl)-2-(5H)-furanone
(85) 3-(3,4-Dibromophenyl)-4-(4-(methylsulfonyl)phenyl)-2-(5H)-furanone
(86) 3-(4-Chloro-3-fluorophenyl)-4-(4-(methylsulfonyl)phenyl)-2-(5H)-furanone
(87) 3-(4-Bromo-3-fluorophenyl)-4-(4-(methylsulfonyl)phenyl)-2-(5H)-furanone
(88) 3-(4-Bromo-2-chlorophenyl)-4-(4-(methylsulfonyl)phenyl)-2-(5H)-furanone
(89) 3-(2-Naphthyl)-4-(4-(methylsulfonyl)phenyl)-2-(5H)-furanone
(90) 3-(7-Quinolinyl)-4-(4-(methylsulfonyl)phenyl)-2-(5H)-furanone
(91) 3-(3,4-Dichlorophenyl)-4-(4-(aminosulfonyl)phenyl)-2-(2H)-furanone
(92) 3-(3,4-Dichlorophenyl)-4-(4-(aminosulfonyl)phenyl)-2-(2H)-furanone
(93) 3-(3,4-Dichlorophenyl)-4-(4-(aminosulfonyl)phenyl)-2-(2H)-furanone
(94) 3-(3-Bromo-4-methoxyphenyl)-4-(4-(aminosulfonyl)phenyl)-2-(2H)-furanone
(95) 3-(4-(Methylsulfonyl)phenyl)-2-phenylbenzo[b]furan
(96) 3-(4-Methylsulfonyl)phenyl)-2-phenylbenzo[b]thiophene
(97) 3-(4-Methylsulfonyl)phenyl-2-phenylinden-1-one
(98) 2-(4-Fluorophenyl)-3-(4-(methylsulfonyl)phenyl)indole
(99) 3-(4-Fluorophenyl)-2-(4-(methylsulfonyl)phenyl)indole
(100) 2-(4-Fluorophenyl)-3-(4-(methylsulfonyl)phenyl)-4H-thieno[2,3-c]-furan-6-one
(101) 2-(3,4-Difluorophenyl)-3-(4-(methylsulfonyl)phenyl)-4H-thieno[2,3-c]-furan-6-one
(102) 2-(4-Fluorophenyl)-3-(4-(aminosulfonyl)phenyl)-4H-thieno[2,3-c]-furan-6-one
(103) 2-(3,4-Difluorophenyl)-3-(4-(aminsulfonyl)phenyl)-4H-thieno[2,3-c]-furan-6-one
(104) 3-(4-(Methylsulfonyl)phenyl)-2-phenyl)-4,7-dihydrothieno[2,3-c]pyran-5-one
(105) 2-(4-(Methylsulfonyl)phenyl)-3-phenyl)-4H-thieno[2,3-c]furan-6-one
(106) 5-(4-(Methylsulfonyl)phenyl)-6-phenylimidazo[2,1-b]thiazole
(107) 2-Methyl-5-(4-(methylsulfonyl)phenyl)-6-phenylimidazo[2,1-b]thiazole
(108) 3-Methyl-5-(4-(methylsulfonyl)phenyl)-6-phenylimidazo[2,1-b]thiazole
(109) 2-Bromo-5-(4-(methylsulfonyl)phenyl)-6-phenylimidazo[2,1-b]thiazole
(110) 3-Trifluoromethyl-5-(4-(methylsulfonyl)phenyl)-6-phenylimidazo[2,1-b]thiazole
(111) 2,3-Dimethyl-5-(4-(methylsulfonyl)phenyl)-6-phenyl-imidazo[2,1-b]thiazole
(112) 5-(4-(Methylsulfonyl)phenyl)-6-(4-fluorophenyl)imidazo[2,1-b]thiazole
(113) 5-Phenyl-6-(4-(methylsulfonyl)phenyl)-imidazo[2,1-b]thiazole
(114) 2-Chloro-5-(4-(methylsulfonyl)phenyl)-6-(4-chlorophenyl)imidazo[2,1-b]thiazole
(115) 2,2-Dichloro-5-(4-(methylsulfonyl)phenyl)-6-(4-chlorophenyl)imidazo[2,1-b]thiazole
(116) 5-(4-(Methylsulfonyl)phenyl)-6-(imidazo[2,1-b]-1,3,4-thiadiazole
(117) 5-Phenyl-6-(4-(methylsulfonyl)phenyl)-imidazo[2,1-b]-1,3,4-thiadiazole
(118) 2-Methyl-5-(4-(methylsulfonyl)phenyl)-6-phenyl-imidazo[2,1-b]-1,3,4-thiadiazole
(119) 2-Methyl-5-phenyl-6-(4-methylsulfonyl)phenyl)-imidazo[2,1-b]-1,3,4-thiadiazole
(120) 5-(4-(Methylsulfonyl)phenyl)-6-(4-fluorophenyl)-imidazo[2,1-b]-1,3,4-thiadiazole
(121) 5-(4-(Methylsulfonyl)phenyl)-6-phenyl-1H-imidazo[2,1-b]-s-thiazole
(122) 5-Phenyl-6-(4-(methylsulfonyl)phenyl)thiazolo[3,2-b]-1,3,4-triazole
(123) 2,3-Dihydro-5-(4-(methylsulfonyl)phenyl)-6-phenylimidazo[2,1-b]thiazole
(124) 2-[(4-Methylthio)phenyl]-1-biphenyl
(125) 1-Cyclohexene-2-(4'-methylsulfonylphenyl)benzene
(126) 3-(4'-Methylsulfonylphenyl)-4-phenylphenol
(127) 1-[2-(4-Methylsulfonylphenyl)phenyl]piperidine
(128) 1-[2-(4'-Methylsulfonylphenyl)phenyl]pyrrole
(129) 1-Phenoxy-2-(4'-methylsulfonylphenyl)benzene
(130) 5-(4-Fluorophenyl)-2-methoxy-4-[4-(methylsulfonyl)phenyl]-6-(trifluoromethyl)pyridine
(131) 2-Ethoxy-5-(4-fluorophenyl)-4-[4-(methylsulfon-yl)phenyl]-6-(trifluoromethyl)pyridine
(132) 5-(4-Fluorophenyl)-4-[4-(methylsulfonyl)phenyl]-2-(2-propynyloxy)-6-(trifluoromethyl)pyridine
(133) 2-Bromo-5-(4-fluorophenyl)-4-[4-(methylsulfon-yl)phenyl]-6-(trifluoromethyl)pyridine
(134) 3-[1-(p-Bromobenzyl)-5-methoxy-2-methylindol-3-yl]propanoic acid
(135) 3-[1-(p-Bromobenzyl)-5-methoxy-2-methylindol-3-yl]butanoic acid, sodium salt
(136) 2-Benzyl-3-[1-(p-bromobenzyl)-5-methoxy-2-methylindol-3-yl-propanoic acid
(137) 3-[1-(p-Bromobenzyl)-5-methoxy-2-methylindol-3-yl]-2,2-dimethylpropanoic acid
(138) 3-[1-(p-Bromobenzyl)-5-methoxy-2-methylindol-3-yl]-4,4,4-trifluorobutanoic acid, sodium salt
(139) trans-2-[1-(p-Bromobenzyl)-5-methoxy-2-methylindol-3-yl]-cyclo-propanecarboxylic acid, sodium salt
(140) 3-[1-(p-Bromobenzyl)-5-methoxy-2-methylindol-3-yl]-hydroxy-2-methyl propanoic acid, sodium salt
(141) [1(1-(p-Bromobenzyl)-5-methoxy-2-methylindol-3-yl]-cyclopropylacetic acid, sodium salt
(142) trans-(+)-2-[1-(p-Bromobenzyl)-5-methoxy-2-methylindol-3-yl]cyclopropanecarboxylic acid, sodium salt
(143) 3-[1-(p-Bromobenzyl)-5-methoxy-2-methylindol-3-yl]-2-methylpropanoic acid and sodium salt
(144) 3-[1-(p-Chlorobenzyl)-5-methoxy-2-methylindol-3-yl]-4,4,4-trifluorobutanoic acid and sodium salt
(145) syn-3-[1-(p-Bromobenzyl)-5-methoxy-2-methylindol-3-yl]-2-methylbutanoic acid
(146) anti-3-[1-(p-Bromobenzyl)-5-methoxy-2-methylindol-3-yl]-2-methylbutanoic acid and sodium salt
(147) 3-[5-(Bromo-1-(p-bromobenzyl)-2-methylindol-3-yl]butanoic acid and sodium salt
(148) (−)-3-[1-(p-Bromobenzyl)-5-methoxy-2-methylindol-3-yl]-butanoic acid and sodium salt (149) (+)-3-[1-(p-Bromobenzyl)-5-methoxy-2-methylindol-3-yl]-butanoic acid and sodium salt
(150) trans-(−)-2-[1-(p-Bromobenzyl)-5-methoxy-2-methylindol-3-yl]cyclopropanecarboxylic acid and sodium salt
(151) 3-[1-(p-Bromobenzyl)-2,5-dimethylindol-3-yl]propanoic acid
(152) 3-[5-(Bromo-1-(p-bromobenzyl)-2-methylindol-3-yl]propanoic acid
(153) 3-[1-(p-Bromobenzyl)-5-chloro-2-methylindol-3-yl)propanoic acid
(154) 3-[1-(p-Chlorobenzyl)-5-methoxy-2-methylindol-3-yl)-2-methylpropanoic acid
(155) Methyl 3-[1-(p-bromobenzyl)-5-methoxy-2-methylindol-3-yl)propanoate
(156) 3-[1-(p-Bromobenzyl)-5-methoxy-2-methylindol-3-yl)-3-methylbutanoic acid
(157) 5-Methanesulfonamido-6-(2,4-difluorophenylthio)-1-indanone
(158) 5-Methanesulfonamido-6-(2,4-dichlorophenoxy)-1-indanone
(159) 2-(4-Chlorophenyl)-4-hydroxy-1-[4-(methylsulfonyl)phenyl]-4-(trifluoromethyl)-4,5-dihydro-1H-imidazole
(160) 2-(4-Chlorophenyl)-1-[4-(methylsulfonyl)phenyl]-4-(trifluoromethyl)-1H-imidazole
(161) 1-(4-Fluorophenyl)-4-hydroxy-2-[4-(methylsulfo-nyl)phenyl]-4-(trifluoromethyl)-4,5-dihydro-1H-imidazole
(162) 1-(4-Fluorophenyl)-2-[4(methylsulfonyl)phenyl]-4-(trifluoromethyl)-1H-imidazole
(163) 2-(4-Chlorophenyl)-1-[4-methylsulfonyl)phenyl]-4-methyl-1H-imidazole
(164) 2-(4-Chlorophenyl)-1-[4-methylsulfonyl)phenyl]-4-phenyl-1H-imidazole
(165) 2-(4-Chlorophenyl)-4-(4-fluorophenyl)-1-[4-(methylsulfonyl)phenyl]-1H-imidazole
(166) 4-(4-Bromophenyl)-2-(4-chlorophenyl)-1-[4-(methylsulfo-nyl)phenyl]-1H-imidazole
(167) 2-(4-Chlorophenyl)-1-[4-(methylsulfonyl)phenyl]-4-(2-naphthyl)-1H-imidazole
(168) 2-(4-Chlorophenyl)-1-[4-(methylsulfonyl)phenyl]-4-[4-(trifluoromethoxy)phenyl]-1H-imidazole
(169) 2,4-Bis(4-chlorophenyl)-1-[4-(methylsulfonyl)phenyl]-1H-imidazole
(170) 2-(4-Chlorophenyl)-4-(3-chlorophenyl)-1-[4-(methylsulfonyl)phenyl]-1H-imidazole
(171) 2-(4-Chlorophenyl)-4-(4-methoxyphenyl)-1-[4-(methylsulfonyl)phenyl]-1H-imidazole
(172) 2-(4-Chlorophenyl)-4-(3-fluorophenyl)-1-[4-(methylsulfonyl)phenyl]-1H-imidazole
(173) 2-(4-Chlorophenyl)-4-[(4-chlorophenoxy)methyl]-1-[4-(methylsulfonyl)phenyl]-1H-imidazole
(174) 2-(3-Chloro-4-methylphenyl)-1-[4-(methylsulfo-nyl)phenyl]-4-(trifluoromethyl)-1H-imidazole
(175) 5-[1-[4-(Methylsulfonyl)phenyl)-4-(trifluoromethyl)-1H-imidazole-2-yl]-1,3-benzodioxole
(176) 2-(3-Fluoro-4-methoxyphenyl)-1-[4-(methylsulfonyl)-phenyl-4-(trifluoromethyl)-1H-imidazole
(177) 2-(4-Chlorophenyl)-4-[(phenylthio)methyl]-1-[4-(methylsulfonyl)phenyl]-1H-imidazole
(178) 2-(4-Chlorophenyl)-4-[(N-methyl-N-phenylamino)methyl]-1-[4-(methylsulfonyl)phenyl]-1H-imidazole
(179) 2-(4-Chlorophenyl)-4-[2-quinolyl)methoxymethyl]-1-[4-(methylsulfonyl)phenyl]-1H-imidazole
(180) 2-(4-Chlorophenyl)-4-methoxymethyl-1-[4-(methylsulfonyl)phenyl]-1H-imidazole
(181) 2-(4-Fluorophenyl)-1-[4-(methylsulfonyl)phenyl]-4-trifluoromethyl-1H-imidazole
(182) 1-[4-(Methylsulfonyl)phenyl]-2-phenyl-4-trifluoromethyl-1H-imidazole
(183) 2-(3-Chloro-4-methoxyphenyl)-1-[4-(methylsulfonyl)phenyl]-4-trifluoromethyl-1H-imidazole
(184) 2-(4-Methylphenyl)-1-[4-(methylsulfonyl)phenyl]-4-trifluoromethyl-1H-imidazole
(185) 1-[4-(Methylsulfonyl)phenyl]-2-(4-trifluoromethyl-phenyl)-4-trifluomethyl-1H-imidazole
(186) 4-[2-(4-Chlorophenyl)-4-(trifluoromethyl)-1H-imidazol-1-yl]benzenesulfonamide
(187) 4-[2-(3-Chloro-4-methylphenyl)-4-(trifluoromethyl)-1H-imidazol-1-yl]benzenesulfonamide
(188) 3-[1-(4-Methylsulfonyl)phenyl]-4-trifluoromethyl-1H-imidazol-2-yl]pyridine
(189) 2-[1-(4-Methylsulfonyl)phenyl]-4-trifluoromethyl-1H-imidazol-2-yl]pyridine
(190) 4-[1-[4-(Methylsulfonyl)phenyl]-4-trifluoromethyl-1H-imidazol-2-yl]pyridine
(191) 2-Methyl-5-[1-[4-(methylsulfonyl)phenyl]-4-trifluoromethyl-1H-imidazol-2-yl]pyridine
(192) 2-Methyl-6-[1-[4-(methylsulfonyl)phenyl]-4-trifluoromethyl-1H-imidazol-2-yl]pyridine
(193) 5-Methyl-2-[1-[4-(methylsulfonyl)phenyl]-4-trifluoromethyl-1H-imidazol-2-yl]pyridine
(194) 4-Methyl-2-[1-[4-(methylsulfonyl)phenyl]-4-trifluoromethyl-1H-imidazol-2-yl]pyridine
(195) 2-Methoxy-5-[1-[4-(methylsulfonyl)phenyl]-4-trifluoromethyl-1H-imidazol-2-yl]pyridine
(196) 4-[2-(6-Methylpyridin-3-yl)-4-(trifluoromethyl)-1H-imidazol-1-yl]benzenesulfonamide
(197) 4-[2-(6-Methylpyridin-2-yl)-4-(trifluoromethyl)-H-imidazol-1-yl]benzenesulfonamide
(198) 3-Methyl-5-[1-[4-(methylsulfonyl)phenyl]-4-(trifluoromethyl)-1H-imidazol-2-yl]pyridine
(199) 4-[2-(4-Methylpyridin-2-yl)-4-(trifluoromethyl)-1H-imidazol-1-yl]benzenesulfonamide
(200) 2-[1-[4-(Methylsulfonyl)phenyl]-4-(trifluoromethyl)-1H-imidazol-2-yl]thiophene
(201) 3-[1-[4-(Methylsulfonyl)phenyl]-4-(trifluoromethyl)-1H-imidazol-2-yl]thiophene
(202) 4-[2-(5-Methylpyridin-3-yl)-4-(trifluoromethyl)-1H-imidazol-1-yl]benzenesulfonamide
(203) 2-Methyl-3-[1-[4-(methylsulfonyl)phenyl]-4-(trifluoro-methyl)-1H-imidazol-2-yl]thiophene
(204) 4-[2-(2-Methylpyridin-3-yl)-4-(trifluoromethyl)-1H-imidazol-1-yl]benzenesulfonamide
(205) 4-[2-Pyridin-3-yl)-4-(trifluoromethyl)-1H-imidazol-1-yl]benzenesulfonamide The synthesis of compounds 1–39 is disclosed in Talley et al. U.S. Pat. No. 5,466,823. The synthesis of compounds 40 and 41 is disclosed in Black et al. U.S. Pat. No. 5,436,265. The synthesis of compounds 42–94 is disclosed in Ducharme et al. U.S. Pat. No. 5,474,995. The synthesis of compounds 95–105 is disclosed in Prasit et al. U.S. Pat. No. 5,521,213. The synthesis of compounds 106–123 is disclosed in Gauthier et al. U.S. Pat. No. 5,552,422. The synthesis of compounds 124–129 is disclosed in Batt U.S. Pat. No. 5,593,994. The synthesis of compounds 130–133 is disclosed in Lee U.S. Pat. No. 5,596,008. The synthesis of compounds 134–156 is disclosed in Lau et al. U.S. Pat. No. 5,604,253. The synthesis of compounds 157 and 158 is disclosed in Guay et al. U.S. Pat. No. 5,604,260. The synthesis of compounds 159–205 is disclosed in Khanna et al. U.S. Pat. No. 5,616,601.

Other selective inhibitors of cyclooxygenase-2 and their syntheses are taught in Examples 2–108, 110–129, 131–150, 152, 301–312, and 401–413 of Batt et al. U.S. Pat. No. 5,593,994, the disclosure of which is incorporated herein by reference. Still other selective inhibitors of cyclooxygenase-2 and their syntheses are taught in Examples 1–11, 13–16, and 18–25 of Guay et al. U.S. Pat. No. 5,604,260, the disclosure of which is incorporated herein by reference. Still other selective inhibitors of cyclooxygenase-2 and their syntheses are taught in Examples 1–13 including Examples 1a–1p and 4a–4h of Talley et al. U.S. Pat. No. 5,633,272, the disclosure of which is incorporated herein by reference. Still other selective inhibitors of cyclooxygenase-2 are taught in Examples 1–131 of Lau et al. U.S. Pat. No. 5,639,780, the disclosure of which is incorporated herein by reference. Still other selective inhibitors of cyclooxygenase-2 are taught in Examples 1–6 of Talley et al. U.S. Pat. No. 5,643,933, the disclosure of which is incorporated herein by reference. Still other selective inhibitors of cyclooxygenase-2 are taught in Examples 1–4 of Lau et al. U.S. Pat. No. 5,510,368, the disclosure of which is incorporated herein by reference.

Another example of a selective inhibitor of cyclooxygenase-2 useful herein are those which directly inhibit the enzyme cyclooxygenase-2 and which also inhibit the synthesis of cyclooxygenase-2 protein and which have antioxidant properties. These cyclooxygenase-2 inhibitors preferably contain phenyl group with two or more substituents selected from the group consisting of hydroxy and $C_{1-4}$-alkoxy (e.g., methoxy) on the phenyl. Specific compounds of this class includes, for example, 4-[5-methyl-3-[[(2,3-hydroxy)phenoxy]methyl]-1H-pyrazol-1-yl]benzenesulfonamide and 4-methyl-5-(4-methylsulfonyl)phenyl-2-[(2,3-hydroxyphenoxy)methyl]oxazole and the corresponding compounds where methoxy or ethoxy replaces hydroxy. These compounds and their syntheses are described in Dannenberg Provisional Application No. 60/069,955 the entire disclosure of which is incorporated herein by reference.

A preferred selective inhibitor of cyclooxygenase-2 for use herein is 4-[5-(4-methylphenyl)-3-(trifluoromethyl)-1H-pyrazol-1-yl]benzenesulfonamide which is compound (4) set forth above. It is believed that this compound is celecoxib (Tradename Celebrex).

Another preferred selective inhibitor of cyclooxygenase is vioxx which is MK-0966; it is compound (63) set forth above.

The dosage of selective inhibitor of cyclooxygenase-2 for the method herein is a cyclooxygenase-2 inhibiting amount which is a therapeutically effective amount. In general, the dosage ranges from 0.1 to 30 mg/kg. The dosages for any particular agent will vary within said range. For compound (4) referred to above, the dosage preferably ranges from 3 to 12 mg/kg.

The route of administration of selective inhibitor of cyclooxygenase-2 is systemic or local for the treatment of sore throat including that caused by tonsillitis or pharyngitis. For systemic administration, the route of administration is preferably oral but other routes of systemic administration, e.g., parenteral such as intravenous, are also useful. For local administration, the selective inhibitor of cyclooxygenase-2 is applied directly to the sore tissue, e.g., formulated as a lozenge, oral rinse or spray.

The route of administration of selective inhibitor of cyclooxygenase-2 is systemic for the treatment sinusitis. Preferably, the route of administration is oral but other routes of systemic administration, e.g., parenteral such as intravenous, are also useful.

We turn now to the cyclooxygenase-2 inhibitors from natural sources. These cyclooxygenase-2 inhibitors from natural sources also inhibit cyclooxygenase-1.

The cyclooxygenase-2 inhibitors from natural sources include, for example, resveratrol, curcumin, caffeic acid phenethyl ester, ursolic acid, carnosol, shikonin and licochalcone A.

Resveratrol has the structure

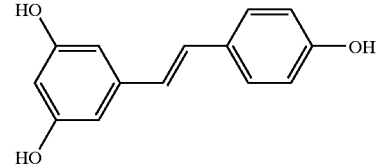

and is found in grapes and other foods. Inhibition by resveratrol of cyclooxygenase-2 transcription and activity is described in Subbaramaiah, K., et al., The Journal of Biological Chemistry, Vol. 273, 21875–21882 (1998).

The inventor herein has published abstracts showing that curcumin and caffeic acid phenethyl ester can inhibit cyclooxygenase-2.

The inhibitors of cyclooxygenase-2 from natural sources are preferably used as topical therapy for sore throats, e.g., tonsillitis and pharyngitis. In such case, the agent is readily administered as a lozenge, oral rinse or spray. In general, the dosages for inhibitors of cyclooxygenase-2 from natural sources used in this way ranges from 1 to 100 mg/kg. For resveratrol, a single application is, for example, 0.25 to 4 grams, administered from one to six times a day as needed.

The inhibitors of cyclooxygenase-2 from natural sources can be administered systemically for the treatment of sore throat or sinusitis. In such case, the route of administration is preferably oral but other routes of administration, e.g., parenteral such as intravenous, are also useful. In general, the dosage of inhibitors of cyclooxygenase-2 from natural sources for systemic administration ranges from 10 to 100 mg/kg and the dosage for resveratrol for systemic administration preferably ranges from 10 to 100 mg/kg.

The treatments are repeated from day-to-day as long as symptoms ameliorate. For tonsillitis, sore throat and pain are ameliorated. For pharyngitis, sore throat and pain on swallowing are ameliorated. For sinusitis, pain in the maxillary area and teeth and frontal headache are ameliorated.

One genus of inflammatory diseases herein constitutes diseases of the head and neck except for periodontitis.

In one embodiment herein, the inflammatory disease of the head and neck is periodontitis and the treating agent is a cyclooxygenase-2 inhibitor from a natural source. Thus, in this case, the method is for treating a patient with periodontitis and comprises administering to said patient a therapeutic amount of a cyclooxygenase-2 inhibitor from a natural source. The cyclooxygenase-2 inhibitors from a natural source are those described above and are preferably used as topical therapy for periodontitis. In such case, the agent is readily administered as a lozenge, oral rinse or spray. In such case, in general, the dosage ranges from 1 to 100 mg/kg. For resveratrol, a single application is, for example, 0.25 to 4 grams, administered one to six times a day. The cyclooxygenase-2 inhibitors from a natural source can also be administered systematically for the treatment of periodontitis. In such case, the route of administration is preferably oral but other routes of administration, e.g., parenteral such as intravenous are also useful. In general, the dosage for systemic administration ranges from 10 to 100 mg/kg, and the dosage for resveratrol for systemic administration preferably ranges from 10 to 100 mg/kg. The treatment is continued from day-to-day, as long as improvement occurs, e.g., as long as decrease in bleeding of gums and stopping of pocket formation and bone loss, occurs.

The invention is indicated and illustrated by the following background and working examples.

Background Example

Patients underwent tonsillectomy because of a history of tonsillitis or obstructive sleep apnea (OSA). Following surgical removal of the tonsils, a 2 mm by 2 mm piece of mucosa was sharply excised with a #15 blade to provide samples for COX-2 mRNA analysis. The mucosa was placed in an autoclaved eppendorf tube and frozen in liquid nitrogen. Levels of COX-2 mRNA in the samples were measured by quantitative reverse-transcription polymerase chain reaction (RT-PCR).

The COX-2 mRNA measurement was carried out as follows:

Frozen tissues were homogenized and total RNA was isolated using RNeasy Mini Kits from Qiagen (Santa Clarita, Calif.). A maximum of 600 ng of total RNA was reverse transcribed using GeneAmp RNA PCR Kit according to the manufacturer's protocol.

Then co-amplification of reverse transcribed cDNA samples and various known amounts of COX-2 mimic was carried out to determine the amount of COX-2 mRNA in a sample.

The COX-2 mimic (competitive PCR deletion construct) for COX-2 was synthesized using a mutant sense primer (nts 932–955 attached to nts 1111–1130 of the human COX-2 gene; 5'-GGTCTGGTGCCTGGTCTGATGATGGAGTGG CTATCACTTCAAAC-3'; the sequence is set forth in the Sequence Listing as SEQ ID NO:1) and an antisense primer (nts 1634–1655 of the human COX-2 gene; 5'-GTCCTTTCAAGGAGAATGGTGC-3'; the sequence is set forth in the Sequence Listing as SEQ ID NO:2), producing a 569-bp PCR product. The mutant sense primer contains the primer-binding sequence of endogenous target (from nt 932 to nt 955 of the human COX-2 gene) attached to the end of an intervening DNA sequence (a 156-bp deletion from nut 956 to nt 1110 of the human COX-2 gene); thus the mimic DNA has primer binding sequences identical to the target cDNA. The 569-bp mimic was further amplified using the sense primer (nts 932–955 of the human COX-2 gene; 5'-GGTCTGGTGCCTGGTCTGATGATG-3'; the sequence is set forth in the Sequence Listing as SEQ ID NO:3) and the antisense primer (5'-GTCCTTTCAAGG AGAATGGTGC-3'; the sequence is set forth in the Sequence Listing as SEQ ID NO:2) in a reaction mixture containing 10 mM Tris-HCl (pH 8.3), 50 mM KCl, 2 mM $MgCl_2$, 0.2 mM deoxynucleotide triphosphate, 2.5 units AmpliTaq DNA polymerase and 400 nM primers for 35 cycles consisting of denaturation at 94° C. for 20 sec, annealing at 60° C. for 20 sec, and extension at 72° C. for 30 sec in a Perkin Elmer 2400 thermal cycler. The PCR products were electrophoresed on 1% agarose gels and gel-purified using GenElute™ Agarose Spin Columns according to the manufacturer's protocol (Supelco, Bellefonte, Pa.).

The co-amplification was carried out as follows: Each PCR was carried out in 25 µl of a reaction mix containing 10 mM Tris-HCl (pH 8.3), 50 mM KCl, 2 mM $MgCl_2$, 0.2 mM deoxynucleotide triphosphate, 2.5 units AmpliTaq DNA polymerase and 400 nM primers (the sense primer: 5'-GGTCTGGTGCCTGGTCTGATGATG-3'; the sequence of which is set forth in the Sequence Listing as SEQ ID NO:3, and the antisense primer: 5'-GTCCTTTCAAGGAG AATGGTGC-3', the sequence of which is set forth in the Sequence Listing as SEQ ID NO:2), 1–10 µl of reverse-transcribed cDNA samples and the various known amounts of COX-2 mimic (between 0.0001 pg and 0.05 pg) adjusted depending on the abundance of the target cDNA. The exact amount of cDNA used for a sample was determined both by the initial total RNA concentration and the relative amounts of COX-2 mRNA on semi-quantitative PCR. The samples were amplified for 35 cycles: denaturation at 94° C. for 30 sec; annealing at 65° C. for 20 sec; extension at 72° C. for 90 sec; and final extension at 72° C. for 15 min. Ten µl of PCR products, 724-bp fragments from endogenous target cDNA and 569-bp fragments from mimic COX-2 were separated by electrophoresis on 1% agarose gels and visualized by ethidium bromide staining.

The results are set forth in Table 1 below wherein "M" stands for male, "F" stands for female, "R" refers to right tonsil, "L" refers to left tonsil, "OSA" stands for obstructive sleep apnea, "h/o" stands for history of and levels of COX-2 are expressed as fg/µg, i.e., as fentograms COX-2 mRNA per microgram total RNA.

TABLE 1

| Case | Age | Gender | Diagnosis | COX-2 mRNA (fg/µg) |
|---|---|---|---|---|
| 1 | 8 | M | OSA | R: 0; L: 0 |
| 2 | 11 | M | OSA | L: 0 |
| 3 | 8 | M | OSA | R: 0; L 0 |
| 4. | 22 | F | recurrent tonsillitis | R: 219; L: 92 |
| 6. | 13 | F | recurrent tonsillitis | R: 105; L: 72 |
| 5. | 27 | F | recurrent tonsillitis | R: 6; L: 48 |
| 7. | 33 | M | h/o tonsillar abscess | R: 92; L: 33 |
| 8. | 12 | M | recurrent tonsillitis | R: 35; L: 60 |

The results show that amounts of COX-2 mRNA were markedly increased in patients with a recent history of tonsillitis compared to tonsils removed for a non-inflammatory condition (obstructive sleep apnea). This result suggests that COX-2 will also be upregulated in other inflammatory diseases of the head and neck, e.g., pharyngitis and sinusitis. Increased amounts of COX-2 would be expected to mediate pain, tissue swelling and inflammation as has been observed in rheumatoid arthritis. Consequently, drugs that inhibit COX-2 will ameliorate the pain, swelling and inflammation.

EXAMPLE I

A 33 year old man has symptoms of a sore throat and fever. He is evaluated by a physician who notes inflamed tonsils and diagnoses tonsillitis. The patient is treated with amoxicillin 500 mg orally every eight hours for ten days. Additionally, he is given Celebrex (celecoxib) 200 mg orally twice a day for seven days. After taking one dose of Celebrex, there is a marked improvement in his throat pain.

EXAMPLE II

A 52 year old woman has symptoms of a sore throat. She is evaluated by her physician who detects an erythematous pharynx. A diagnosis of viral pharyngitis is made. She is given and sucks on lozenges containing 100 mg of Celebrex (celecoxib) four times a day with complete resolution of her sore throat within two days.

EXAMPLE III

A 28 year old woman presents to her physician complaining of fever and headache. On physical examination, she has tenderness over her maxillary sinus. A diagnosis of sinusitis is made. The patient is treated with amoxicillin 500 mg orally every eight hours for ten days. She is also given Celebrex 200 mg orally twice a day for seven days. After taking one dose of Celebrex, there is a marked improvement in her sinus pain.

EXAMPLE IV

A 23 year old woman has symptoms of a sore throat. She purchases lozenges containing 1 gram of resveratrol per lozenge. The subject sucks on four lozenges per day for two days with rapid relief of her throat discomfort.

EXAMPLE V

A 65 year tobacco-smoking male is referred to a periodontist for bleeding gums and is diagnosed with periodontitis. The patient is advised to use resveratrol lozenges containing 1 gram resveratrol twice a day. Four months later, the patient returns and reports markedly decreased bleeding in his gums and improvement in periodontal disease is detected on examination.

Variations

Many variations of the above will be obvious to those skilled in the art. Thus, the invention is defined by the claims.

What is claim is:

1. A method for treating a patient with an inflammatory disease of the head and neck selected from the group consisting of sinusitis, periodontitis, and sore throat caused by tonsillitis or by pharyngitis, comprising a administering to said patient a therapeutic amount of a selective inhibitor of cyclooxygenase-2 or of a cyclooxygenase-2 inhibitor from natural source.

2. The method of claim 1 wherein the disease is not periodontitis.

3. The method of claim 2 wherein the disease is a sore throat caused by tonsillitis or by pharyngitis and the treating agent is a cyclooxygenase-2 inhibitor from a natural source which is topically administered.

4. The method of claim 3 wherein the treating agent is resveratrol.

5. The method of claim 3 wherein the disease is a sore throat that is caused by tonsillitis.

6. The method of claim 3 wherein the disease is a sore throat that is caused by pharyngitis.

7. The method of claim 2 wherein the disease is a sore throat that is caused by tonsillitis or by pharyngitis and the treating agent is a selective inhibitor of COX-2.

8. The method of claim 7 wherein the treating agent is celecoxib.

SEQUENCE LISTING

```
<160> NUMBER OF SEQ ID NOS: 3

<210> SEQ ID NO 1
<211> LENGTH: 44
<212> TYPE: DNA
<213> ORGANISM: Artificial Sequence
<220> FEATURE:
<221> NAME/KEY: misc_feature
<223> OTHER INFORMATION: Description of Artificial Sequence: mutant
      sense primer; nts 932- 955 of COX-2 gene attached to nts 1111-1130
      of COX-2 gene

<400> SEQUENCE: 1
ggtctggtgc ctggtctgat gatggagtgg ctatcacttc aaac                    44

<210> SEQ ID NO 2
<211> LENGTH: 22
<212> TYPE: DNA
<213> ORGANISM: Artificial Sequence
<220> FEATURE:
<221> NAME/KEY: misc_feature
<223> OTHER INFORMATION: Description of Artificial Sequence: antisense
      primer; nts 1634-16 55 of COX-2 gene

<400> SEQUENCE: 2
gtcctttcaa ggagaatggt gc                                            22

<210> SEQ ID NO 3
<211> LENGTH: 24
<212> TYPE: DNA
<213> ORGANISM: Artificial Sequence
<220> FEATURE:
<221> NAME/KEY: misc_feature
<223> OTHER INFORMATION: Description of Artificial Sequence: sense
      primer; nts 932-955 of COX-2 gene

<400> SEQUENCE: 3
ggtctggtgc ctggtctgat gatg                                          24
```

9. The method of claim 7 wherein the treating agent is vioxx.

10. The method of claim 2 wherein the disease is sinusitis and the treating agent is a selective inhibitor of cyclooxygenase-2 which is administered systemically.

11. The method of claim 2 wherein the disease is a sore throat that is caused by tonsillitis or by pharyngitis and the treating agent is selective inhibitor of cyclooxygenase-2 which is topically administered.

12. The method of claim 1 wherein the disease is periodontitis and the treating agent is cyclooxygenase-2 inhibitor from a natural source.

13. The method of claim 1 wherein the inflammatory disease of the head and neck is selected from the group consisting of periodontitis and sore throat caused by tonsillitis or by pharyngitis.

14. The method of claim 1 wherein the inflammatory disease of the head and neck is selected from the group consisting of periodontitis and sore throat caused by tonsillitis.

15. A method for treating a patient with a sore throat comprising administering to said patient a therapeutic amount of a cyclooxygenase-2 inhibitor from a natural source which is topically administered.

16. The method of claim 15 wherein the cyclooxygenase-2 inhibitor from a natural source is administered as a lozenge.

17. The method of claim 16 wherein the cyclooxgenase-2 inhibitor from a natural source is selected from the group consisting of resveratrol, curcumin, caffeic acid phenethyl ester, ursolic acid, carnosol, shikonin and licochalcone A.

* * * * *